United States Patent [19]

Newell et al.

[11] Patent Number: 5,035,237
[45] Date of Patent: Jul. 30, 1991

[54] DEVICES FOR ADMINISTERING MEDICAMENTS TO PATIENTS

[76] Inventors: Robert E. Newell, 21 The Glen, Pinner, Middlesex; Paul K. Rand, 29 Kipling Close, Hitchin, Hertfordshire; Robert A. Fitzsimmons, The Old Vicarage, Egglestone, Barnard Castle, Durham, all of England

[21] Appl. No.: 290,628

[22] Filed: Dec. 27, 1988

Related U.S. Application Data

[62] Division of Ser. No. 891,536, Jul. 29, 1986, Pat. No. 4,811,731.

[30] Foreign Application Priority Data

Jul. 30, 1985 [GB] United Kingdom ............... 8519141
Oct. 10, 1985 [GB] United Kingdom ............... 8525067

[51] Int. Cl.⁵ ............................................. A61M 15/00
[52] U.S. Cl. ............................. 128/203.15; 128/203.21
[58] Field of Search ................... 128/203.15, 203.21; 221/25, 31; 222/81, 83, 87

[56] References Cited

U.S. PATENT DOCUMENTS

| 1,383,270 | 6/1921 | Henning | 222/83 |
| 2,386,877 | 10/1945 | Neilson Jr. et al. | 222/83 |
| 3,888,253 | 6/1975 | Watt et al. | 128/203.21 |
| 3,949,751 | 4/1976 | Birch et al. | 128/203.21 |
| 4,384,649 | 5/1983 | Brodsky | 206/603 |
| 4,444,610 | 4/1984 | Torterotot et al. | 206/603 |
| 4,446,862 | 5/1984 | Baum et al. | 128/203.15 |
| 4,627,432 | 12/1986 | Newell et al. | 128/203.21 |
| 4,690,279 | 9/1987 | Hochberg | 221/25 |

FOREIGN PATENT DOCUMENTS

| 2835135B2 | 2/1980 | Fed. Rep. of Germany. | |
| 6553 | 11/1907 | United Kingdom | 128/203.21 |
| 7525 | 11/1907 | United Kingdom | 128/203.21 |
| 1387954 | 3/1975 | United Kingdom .· | |
| 2178965 | 2/1987 | United Kingdom | 128/203.15 |

Primary Examiner—Edgar S. Burr
Assistant Examiner—Aaron J. Lewis
Attorney, Agent, or Firm—Darby & Darby

[57] ABSTRACT

A device is provided for administering medicaments in solid finely divided form to patients. The device comprises a housing, a tray mounted in the housing and movable between first and second positions relative to the housing, a support disc provided on the tray and adapted to receive a carrier provided with at least one medicament container. A plunger is operable to penetrate a container registered therewith to open the container, movement of the tray from its first to its second position being such as to cause the support to bring a container into registration with the plunger. Air enters through an air inlet and there is an outlet through which a patient can inhale air having medicament therein.

14 Claims, 7 Drawing Sheets

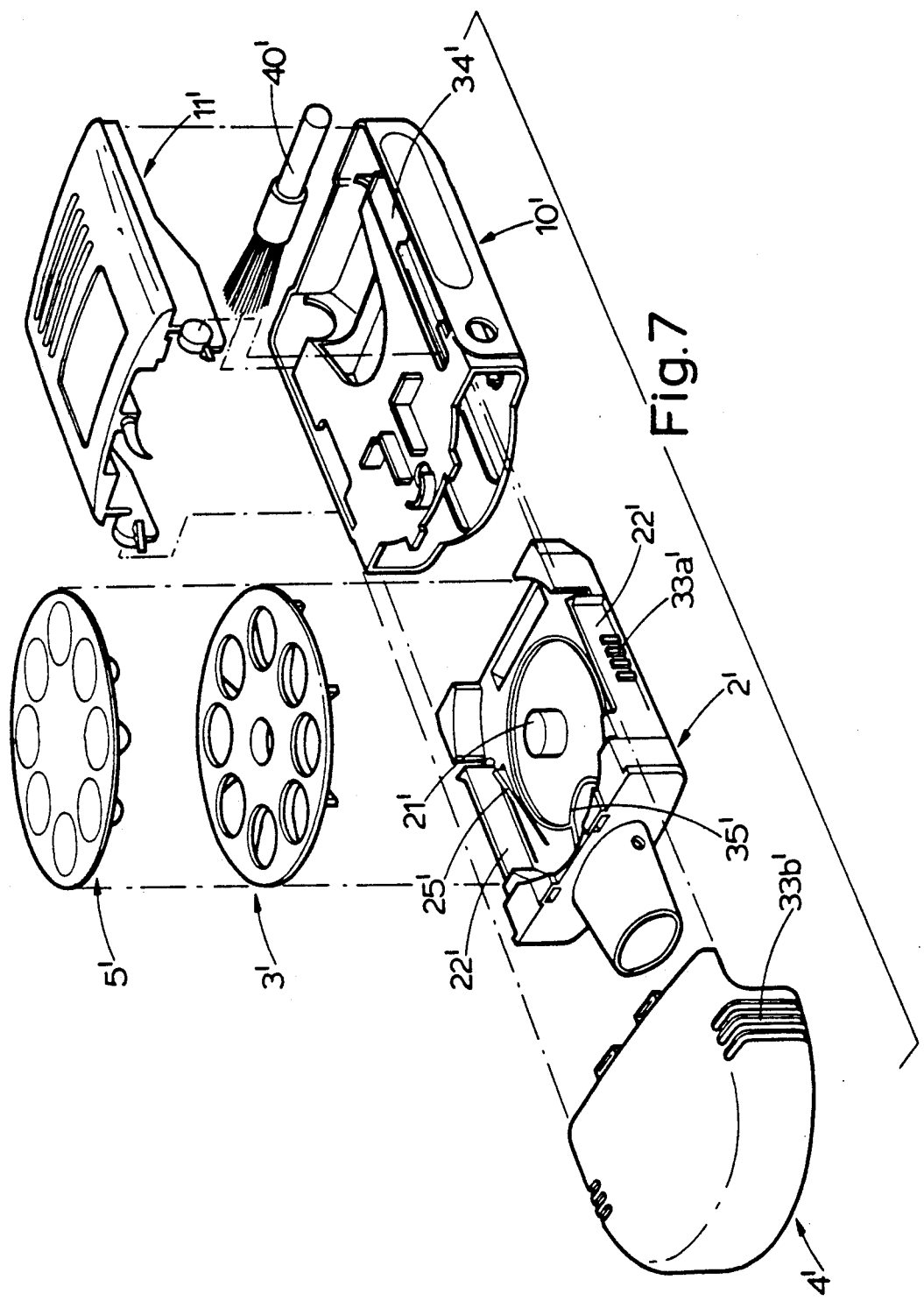

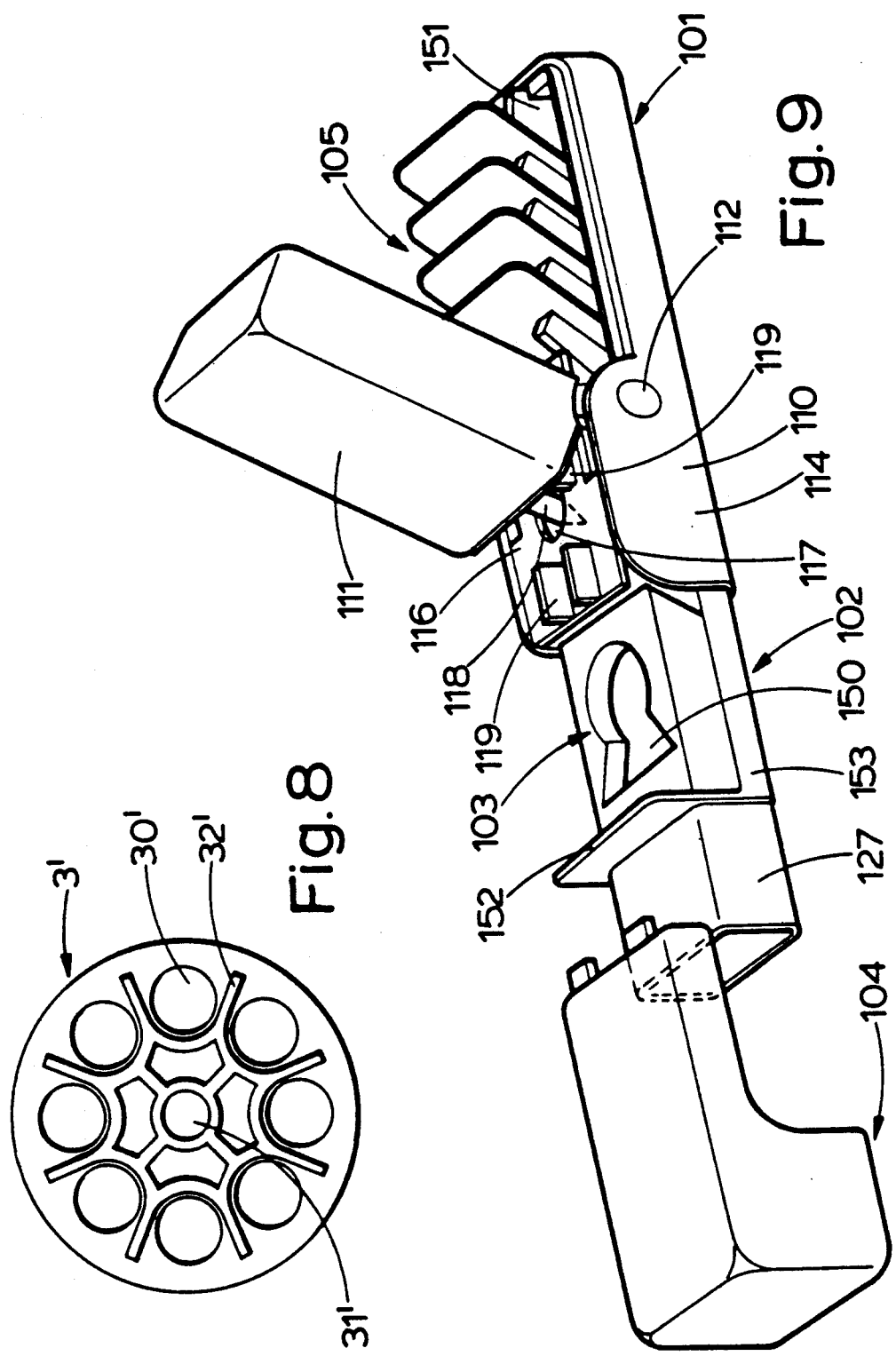

DEVICES FOR ADMINISTERING MEDICAMENTS TO PATIENTS

This is a division of application Ser. No. 891,536 filed July 29, 1986, now U.S. Pat. No. 4,811,731, 8/14/89.

This invention relates to devices by which a medicament in solid finely divided form can be administered to or by patients inhaling through the devices. Such devices are now quite well known for administering medicaments contained in capsules to patients suffering from bronchial conditions such as, for example, bronchial asthma. It is well known for medicament in powder or other finely divided form to be supplied in capsules which are loaded by a patient into such a device. The medicament is then released from the capsule and inhaled by the patient, usually through the mouth, but sometimes through the nose.

The specification of PCT Application Publication No. WO82/01470, GB-A-1387954 and GB-A-2061735 all describe devices for dispensing medicament in finely divided form from capsules. In each of these previously described devices, the capsules are mounted on a rotatable support member on which each capsule in turn can be brought to a position in which it is opened to enable medicament to exit from the capsule to permit it to be inhaled by a patient inhaling through a mouthpiece of the device.

There are disadvantages in the use of capsules, which are made of gelatin, to contain medicaments. Gelatin is relatively unstable and is lacking in physical strength so that the capsules need to be protected by packaging, for example in glass bottles. Environmental degradation of both the capsules and their contents may occur in a relatively short time.

In the device described in UK Patent Specification 1387954 the capsules are mounted in what is referred to therein as a blister pack, and is in fact a plurality of capsules mounted in a blister pack on a rotor which is designed to spin during exhalation by the patient to throw medicament out of an opened capsule, whereafter the patient inhales. This has a number of disadvantages, including the fact that the exhalation which is required is more difficult for some patients, for example asthma patients, than inhalation.

In our patent specification GB-A-2129691 we provided a more convenient way of administering medicament to such patients than had been possible hitherto and which avoided the need to pack medicaments in capsules. The device there described makes use of the technique of packaging a medicament by loading the medicament directly into a blister pack comprising a sheet, which may be laminated, of foil or plastics material which acts as a carrier and which is provided with a number of breakable or openable containers called "blisters" incorporating a sheet secured on a first sheet to form a cover or lid. Such blister packs are in common use with tablets of one kind or another, but we have discovered that they can also be used with medicaments in finely divided solid form. GB-A-2129691 provides a device for administering to patients medicaments in blister pack form.

However, the embodiments described in GB-A-2129691 are more bulky than is desirable. It is an object of the present invention to provide a device which avoids or mitigates this problem.

Attention is also directed to our specification GB-A-2142246 which describes various alternative devices for administering medicaments held in solid finely divided form in blister packs.

According to the present invention there is provided a device for administering medicaments in solid finely divided form to patients, comprising a housing; a tray mounted in the housing and movable between first and second positions relative to the housing; a support provided on the tray and adapted to receive, in use, a carrier provided with at least one medicament container; a plunger operable, in use, to penetrate a container registered therewith to open the container, movement of the tray from its first to its second position being such as to cause in use, the support to bring a container into registration with the plunger; an air inlet through which in use, air can enter the device, and an outlet through which a patient can inhale, whereby medicament will be released from an opened container and entrained in an air flow produced by the patient, air entering the air inlet and passing out through the outlet having entrained medicament therein.

In an embodiment of the invention the support is rotatably mounted on the tray and the carrier has a plurality of medicament containers arranged in a circle. Indexing means are preferably provided so that movement of the tray from its first to its second position causes the support to be indexed to bring the next container into registration with the plunger.

The housing of the device preferably has a base member and a lid pivotally mounted thereon for movement between a closed position and an open position. The plunger can then be carried by the lid and arranged to penetrate a container when the lid is moved to its open position.

The device of the invention is suitable for administering a variety of medicaments such as, for example, salbutamol, beclomethasone dipropionate and sodium cromoglycate.

A significant number of asthma patients suffer from asthma with a severity such that they need to take not one but two medicaments. These are, respectively, a $\beta$-stimulant, for example salbutamol or sodium cromoglycate, and an anti-inflammatory steroid, for example beclomethasone dipropionate. Typically a patient needing both these medicaments will take alternate doses of the two medicaments at prescribed intervals during the day.

It is an object of one aspect of the present invention to provide a single device from which two medicaments can be administered. The two medicaments concerned may be a $\beta$-stimulant and an anti-inflammatory steroid respectively, or some other pair of medicaments used in treating asthma, or some other pair of medicaments inhaled for the purpose of treating some other condition. The reference to two medicaments is to be understood as including not only a pair of medicaments containing two different active ingredients, but also a pair of medicaments containing the same active ingredient in different dosages.

According to this aspect of the present invention there is provided a device according to the invention in tandem with another such device to form a single article.

Some embodiments of the invention are illustrated in the accompanying schematic drawings in which:

FIG. 7 is an exploded perspective view of a second embodiment of the invention;

FIG. 8 is an underplan view of the rotatable support used in the device of FIG. 7;

FIG. 9 is a perspective view of a third embodiment of the invention with the cover removed;

Figure 1:
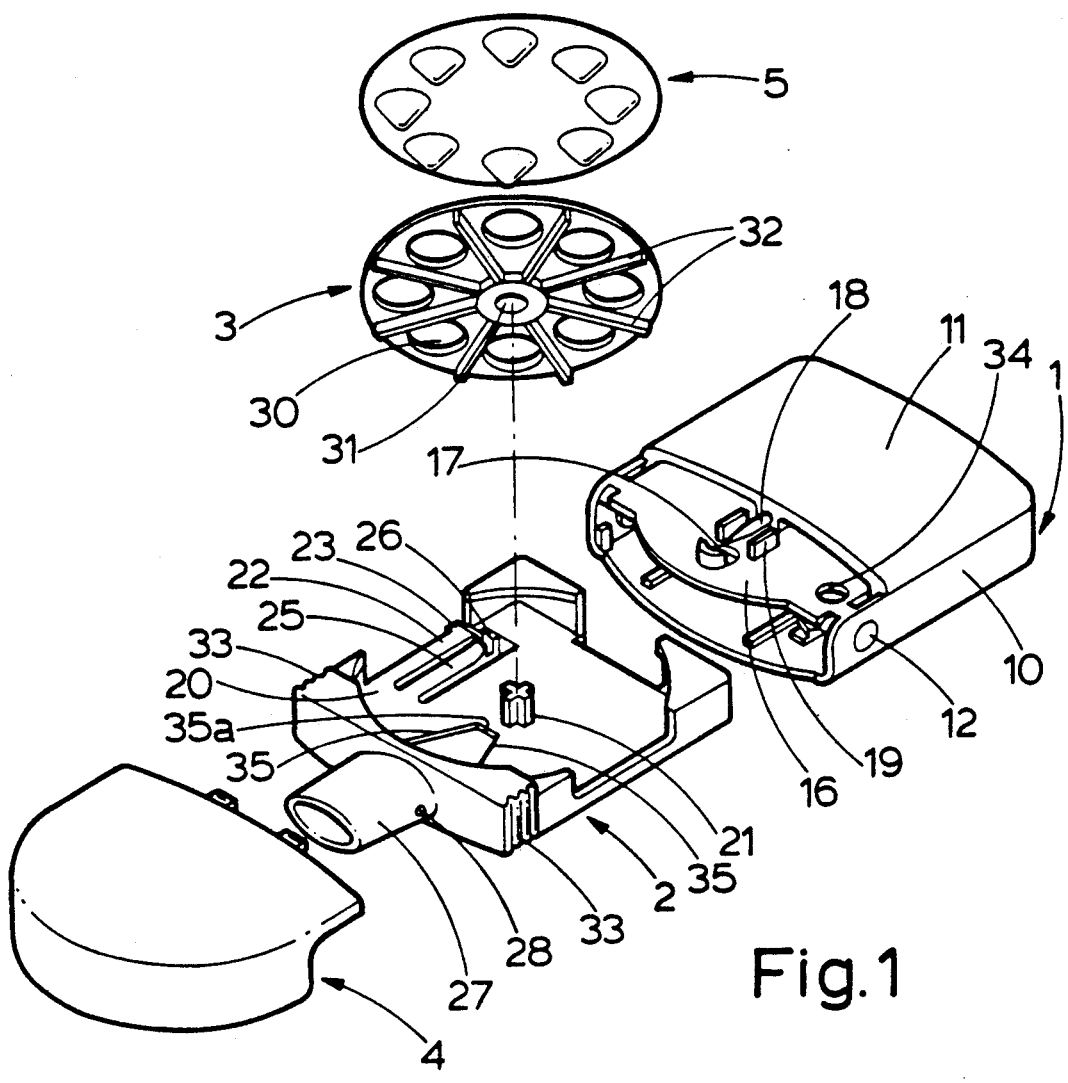
FIG. 1 is an exploded perspective view of a device according to one embodiment of the invention.

The device shown in FIGS. 1 to 6 comprise four principal components, namely a housing 1, a tray 2, a rotatable support 3 and a cover 4. The support 3 is designed to receive a circular blister pack 5, as described in more detail below.

Considering first the housing 1, this comprises a base member 10 and a lid 11 hinged thereto by pivots 12. The base member 10 has a base wall 13, upstanding side and rear walls 14 and 15 and a top wall 16 which extends over only the forward portion of the base member to form a kind of bridge. The top wall 16 has an aperture 17 formed therein. Extending forwardly from the front edge of the lid 11 is an elongated plunger 18. This is so positioned that when the lid 11 is raised the plunger passes through the aperture 17 which also acts as an air inlet into the device. The plunger is conveniently tapered at the tip to form a relatively sharp point, but this is not essential and a blunter plunger would serve the intended purpose which is described below. When the lid is in its lowered position the plunger 18 is protected from damage by upstanding walls 19 formed on the upper wall 16.

Figure 2:
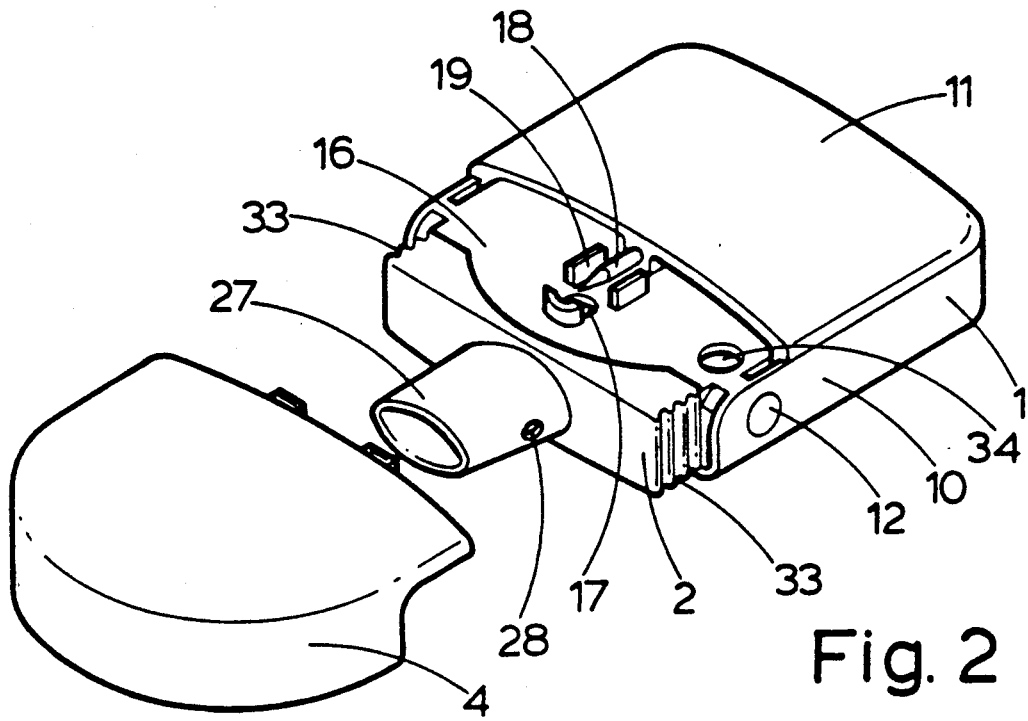
FIG. 2 is a perspective view of the device of FIG. 1 with a cover thereof removed.
Figure 3:
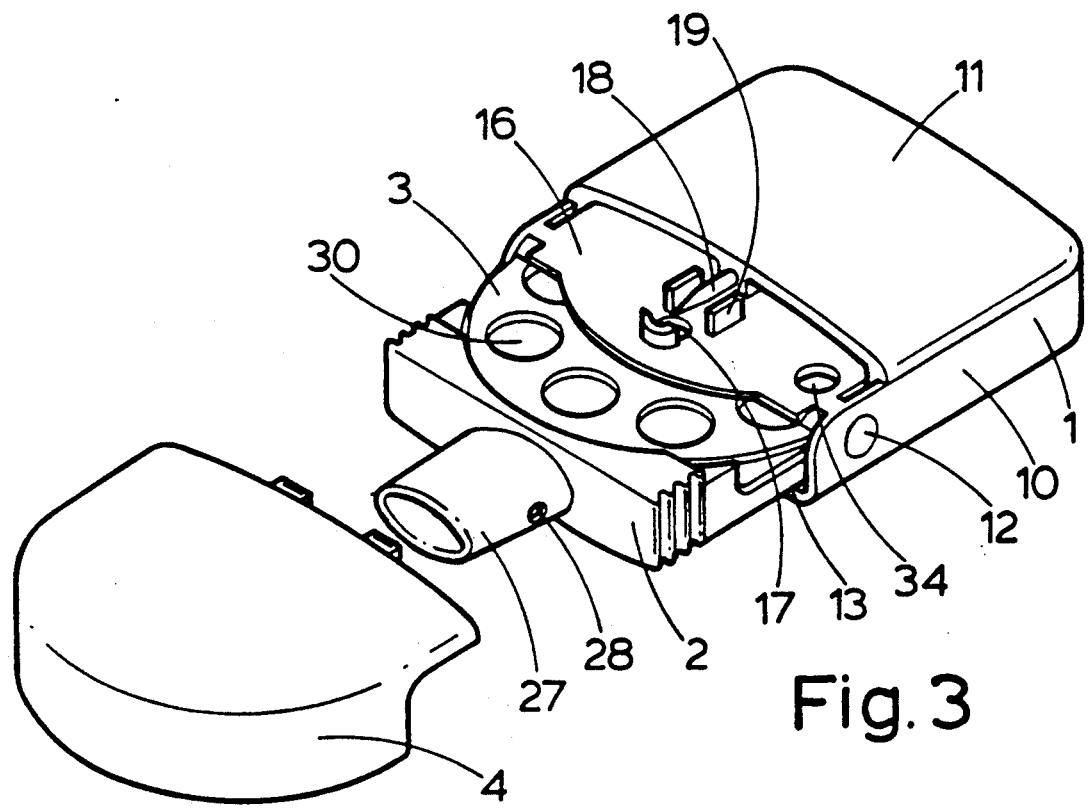
FIG. 3 is a view similar to that of FIG. 2 but with a tray portion thereof in an outward position.
Figure 4:
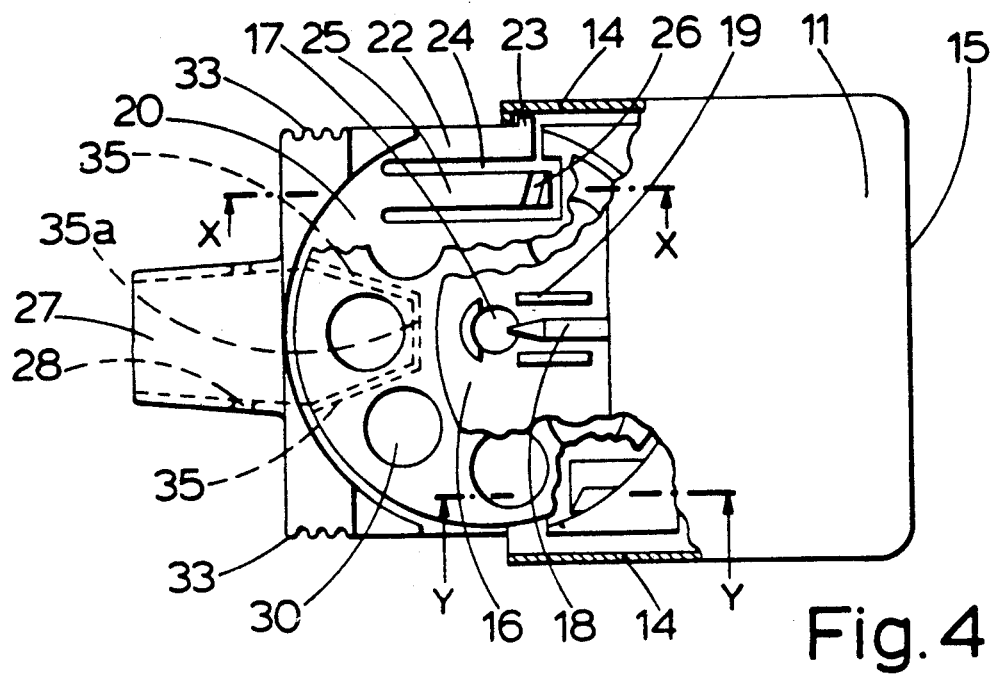
FIG. 4 is a plan view of the device with a portion broken away.
Figure 5:
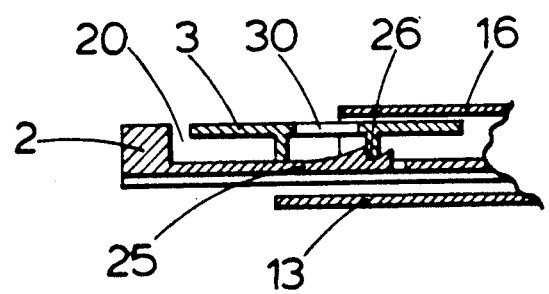
FIG. 5 is a section taken on line X—X in FIG. 4.
Figure 6:
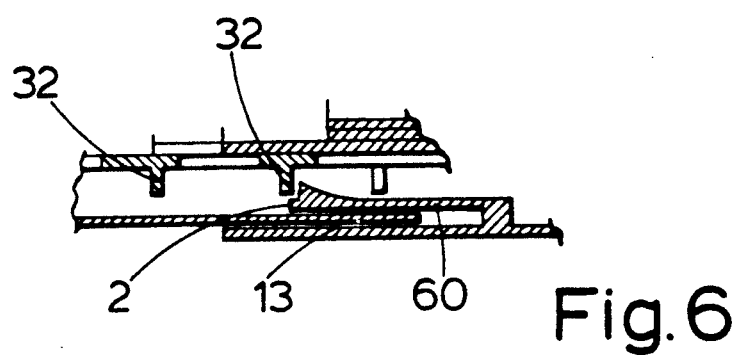
FIG. 6 is a section taken on line Y—Y in FIG. 4.

The tray 2 defines a shallow chamber 20 for receiving the rotatable support 3. In the centre of the chamber 20 is anupstanding lug 21 on which the support 3 is mounted for rotation. The lug 21 is shown as being cruciform in cross-section, but need not be; a lug of circular cross-section, for example, could be used instead. The tray 2 can be moved in the housing between an inward position, as shown in FIG. 2, and an outward position, as shown in FIGS. 3 and 4. Further outward movement beyond the above mentioned outward position is normally prevented by a lug 23 which is formed on the end of an arm 22 and which engages behind an inwardly directed protrusion on one of the side walls 14 of the housing 1. The arm 22 is secured to the rest of the tray only at its forward end and is substantially separated from the rest of the tray by a slot 24. The arm 22 is resilient, and when it is desired to remove the tray completely from the housing this can be achieved by pressing the arm 22 inwardly and then withdrawing the tray. Withdrawal is assisted by the provision of thumb grips 33, in the form of ribs, on both sides of the tray. The tray also has a tongue 25 which can be depressed downwardly, as described below, and which has an open slot 26.

Extending from the front of the tray 2 is a mouthpiece 27. It is through this mouthpiece that medicament leaves the device as it is inhaled by a patient. To improve airflow through the mouthpiece it may be provided with a pair of apertures 28.

The rotatable support 3 is in the form of a disc in which is formed a circular array of circular openings 30. A central opening 31 enables the carrier to be mounted for rotation on the lug 21. A corresponding plurality of ribs 32 are formed on the underside of the support 3, with one rib extending between each two adjacent openings 30.

In use, the cover 4 is removed and the tray with the support 3 mounted thereon, is then removed completely from the housing 1 after the arm 22 has been depressed. A blister pack 5 is then mounted on the support 3 with one blister extending into each of the openings 30. The tray, support and blister pack are then inserted together into the housing. The cover 4 is then replaced. When a patient desires to inhale medicament he removes the cover and raises the lid 11 so as to cause the plunger 18 to pass through the aperture 17 and puncture a respective blister located immediately below the aperture 17. The lid is then lowered to withdraw the plunger from the blister, leaving a hole therein, and the patient inhales the medicament through the mouthpiece 27. It should be noted that the plunger is positively withdrawn from the blister by the patient rather than being left to withdraw under spring pressure (as in GB-A-2129691 mentioned above) which avoids any risk of the plunger remaining jammed in the blister. Either before replacing the cover, or on the next occasion when the patient desires to use the device, the support 3 is rotated to bring the next blister beneath the aperture 17. This is achieved as follows. The tray 2 is withdrawn to its outward position and then pushed back to its inward position. During the latter movement an arm 60 which extends forwardly in the casing 1 and is secured to the base wall 13 thereof engages one of the ribs on the underside of the support 3. This causes the support to rotate in a clockwise direction, as viewed in FIG. 4, by an amount sufficient to bring the next blister beneath the aperture 17. During this rotational movement another of the ribs bears against, and progressively depresses, the tongue 25 until that rib engages in the slot 26 which retains the support in its desired position and prevents further rotation. It will be seen from FIG. 5 that on either side of the slot 26 are a pair of sloping shoulders, the larger of which prevents anticlockwise rotation of the support 3, and the smaller of which is sufficient to normally retain the rib in the slot 26 but which is not such as to prevent the rib leaving the slot on the next occasion when the support 3 is rotated as described above.

The upper surface of the blister pack 5 carries a series of numbers, arranged in a circle, corresponding to the number of blisters in the pack (in this case the numbers 1 to 8). The top wall 16 of the housing 1 has an aperture 34 through which a respective one of the numbers is visible to indicate the number of the blister then aligned with the aperture 17, and hence to indicate how many blisters are left for use, or alternatively how many blisters have been used.

In order to assist in providing maximum efficiency of powder entrainment, means are provided for ensuring an air flow path through the device which is substantially isolated from the surrounding environment. To this end, the tray 2 is provided adjacent the mouthpiece with a pair of upstanding walls 35 which converge towards the centre of the tray, the radially inner ends of the walls 35 being interconnected by a wall 35a. When the support 3 is in a position in which a blister is aligned with the plunger, two adjacent ribs 32 of the support are aligned with the wall 35 and in close contact therewith. Also, the blister pack 5 is in close contact with the underside of the top wall 16 of the tray, at least in the vicinity of the aperture 17. Thus when the patient inhales through the mouthpiece 27 substantially the only air flow which is produced is one which passes through the aperture 17, through the hole formed in the blister aligned therewith, through a chamber defined by the wall 35 and the ribs 32 in contact therewith and thence through the mouthpiece 27, optionally supplemented by air flowing into the mouthpiece through the apertures 28 if these are provided.

There is thus no requirement for airtightness in other parts of the device, for example, airtightness between the housing parts 10 and 11 or between the housing and the tray, and such airtightness is not provided.

Although not visible in the drawings, the device shown in FIGS. 1 to 6 is preferably provided with a recess, located inwardly of the rear wall 15 and extending parallel thereto, for removably receiving a brush which the patient can use to clean the device of powdered medicament spilt therein.

The device shown in FIGS. 1 to 6 may be modified in various ways. For example, the plunger 18 may be curved, as viewed in side elevation so that as it pierces a blister it produces in it a hole which is smaller and more nearly circular than that which is produced if the plunger is straight as illustrated. This provides for improved entrainment of powdered medicament in the air flow produced by inhalation and helps to avoid powder being trapped in the blister. This and other modifications are shown in FIGS. 7 and 8 which illustrate a second embodiment of the invention.

The embodiment of FIGS. 7 and 8 is broadly similar to that of FIGS. 1 to 6, and the reference numerals in FIGS. 7 and 8 are the same as in FIGS. 1 to 6, where appropriate, but with the addition of a prime. Because of the similarities between the two embodiments the following description deals only with features of FIGS. 7 and 8 which differ from the corresponding features of FIGS. 1 to 6.

(a) The arm 22 is replaced by a pair of resilient arms 22', one on either side. The symmetry thus achieved makes it easier to slide the tray 2' in and out.

(b) There is no slot 26. Instead, the ribs 32' on the underside of the disc 3' engage behind the rear edge of tongue 25'.

(c) The walls 35 and 35a are replaced by a smoothly continuous wall 35' in which straight wall 35a is replaced by an arcuate wall portion the ends of which merge into the radially inner ends of the walls 35. A corresponding modification is required in the ribs on the underside of the rotatable support, and FIG. 8 is an underplan view of such a modified support.

(d) The lug 21' is circular in cross-section, rather than being cruciform as shown in FIG. 1.

(e) The thumb grips 33 are replaced by thumb grips 33a' on the arms 22' and additional thumb grips 33b' are provided on the cover 4'.

(f) The aperture 34, through which numbers on the blister pack are visible is replaced by a slot 34'. Most of the slot is covered by the lid 11', but the forward portion is not, and it is through this forward portion that the numbers are visible.

(g) The brush, which is referred to above but is not shown in FIGS. 1 to 6 is shown in FIG. 7 and denoted by reference numeral 40.

FIG. 9 shows a second embodiment of the invention, which instead of using a blister pack comprising a plurality of blisters, uses a plurality of individual packs each containing a single blister. In FIG. 9 components which are comparable in function to those of FIGS. 1 to 6 are denoted by the same reference numerals plus 100.

The device of FIG. 9 comprises a housing 101, a tray 102 with an integral support 103, a cover 104, and a plurality of individual blister packs 105. The housing 101 comprises a base member 110 and a lid 111 hinged thereto by pivots 112. The base member 110 includes side walls 114 and a top wall 116 which extends over only the forward portion of the base member to form a kind of bridge. Extending forwardly from the lid 111 is an elongate plunger 118 which is so positioned that when the lid 111 is raised the plunger passes through an aperture 117 formed in the top wall 116. When the lid is in its lowered position the plunger 118 is protected from damage by upstanding walls 119 formed on the top wall 116.

The blister packs are removably contained in a magazine 151 which is fixed or removable and is located at the rear of the housing 101 and normally covered by the lid 111. In the illustrated embodiment the magazine is arranged to contain four packs, but other sizes of magazine could be used instead.

The tray 102 defines a recess 150 adapted to receive one of the blister packs 105. The recess communicates at its forward end with a mouthpiece 127. The tray is slidable between the outward position illustrated and an inward position in which a flange 152 thereof rests against the forward end of the housing 101. Sliding movement is achieved by means of a pair of runners 153 which pass down the inside of the housing adjacent the side walls 114 thereof. The sides of the magazine 151 stop short of the side walls 114 to permit the runners to pass.

In use, the patient removes the cover 104 and, with the tray in either its inward or outward position, raises the lid 111, and removes a blister pack 105 from the magazine 151. With the tray in its outward position, the patient then places the blister pack on the tray with blister thereof extending downwardly into the recess 150. The lid is then lowered. The tray is then pushed to its inward position and the lid raised, to cause the plunger 118 to puncture the blister, and then lowered. The patient then inhales through the mouthpiece 127, medicament from the blister being entrained in the air flow thus produced. The blister pack is in close contact with the underside of the top wall 116 so that substantially the only air flow is that which passes through the aperture 117, through the hole formed in the blister aligned therewith, through the recess 150 and thence through the mouthpiece 127. If desired, the mouthpiece 127 could be provided with apertures corresponding to the apertures 28 of FIG. 1.

Figure 10:
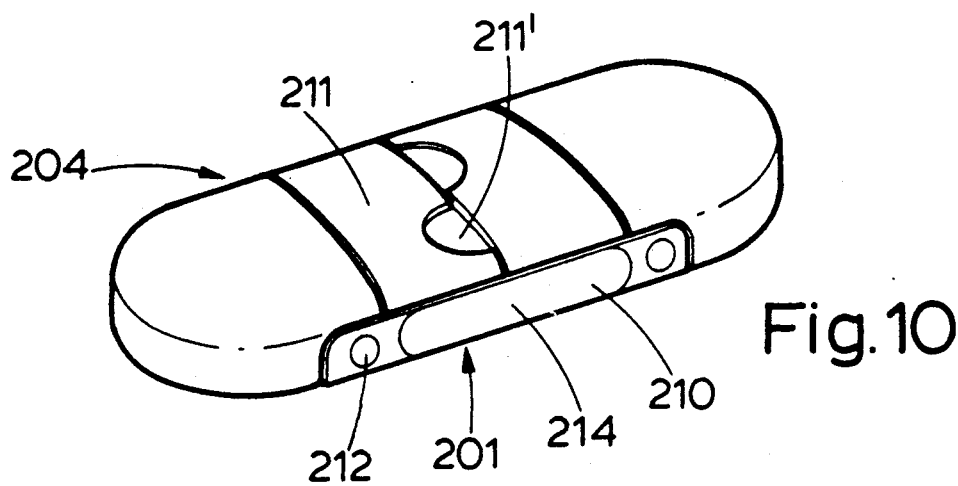
FIG. 10 is a perspective view of a fourth embodiment of the invention, for use in dispensing two medicaments.
Figure 11:
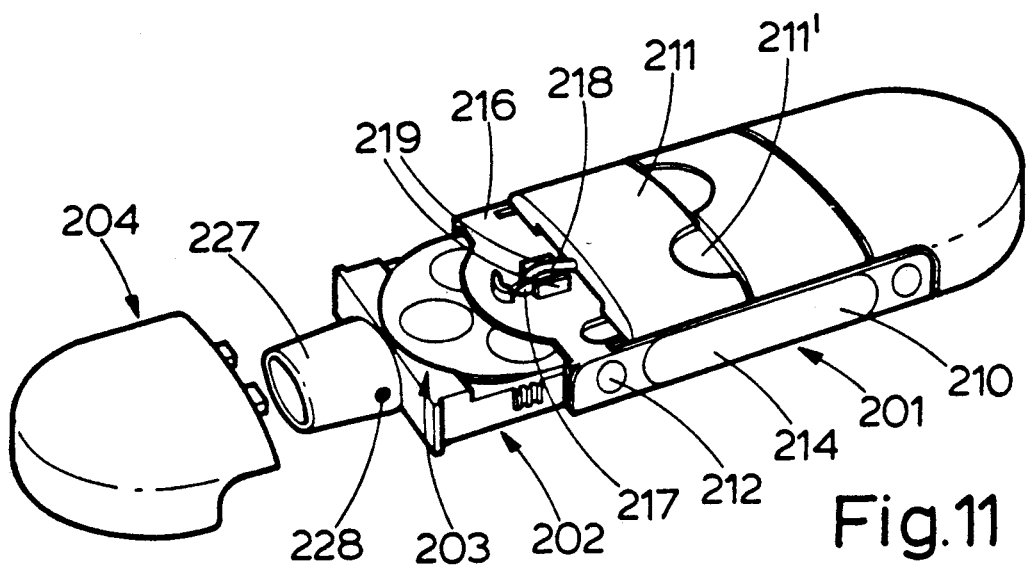
FIG. 11 is a perspective view of the article of FIG. 10 with a cover thereof removed and with a tray portion thereof in an outward position.
Figure 12:
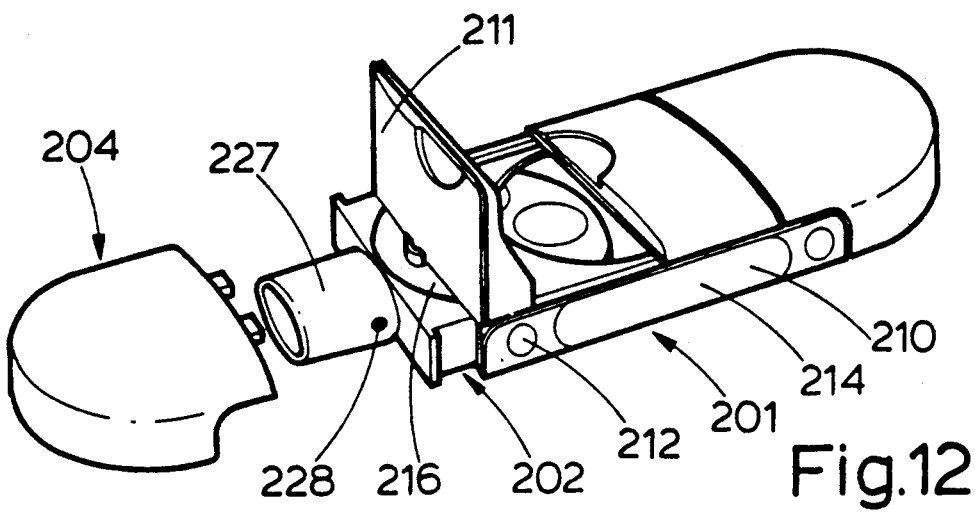
FIG. 12 is a perspective view of the article of FIG. 10 with one of the covers thereof removed and with a lid thereof in a raised position.

The embodiment of FIGS. 10 to 12 comprises a pair of identical inhalation devices arranged back to back to form a single article. Each device comprises a housing 201, a tray 202, a rotatable support 203 and a cover 204. The support 203 is designed to receive a circular blister pack which, for use in the embodiment illustrated in FIGS. 10 to 12, comprises four blisters arranged in a circle. It is to be understood, however, that blister packs with other numbers of blisters could be used instead, given appropriate modification to the rotatable support 203.

Considering first the housing 201, this comprises a base member 210 which is common to each of the devices. The housing further comprises a lid 211 hinged to the base member 210 by pivots 212. Each device has its own lid. The lid 211 has a recess 211' is the upper surface thereof, the recess in one side making it easier for a patient to lift the other lid.

The recesses of the two lids are offset from one another on opposite sides of the article. The base member 210 has a base wall (not visible in the drawings), upstanding side walls 214, and a pair of top walls 216, one in each device, each top wall 216 being arranged to form a bridge between the side walls. Each top wall 216 has an aperture 217 formed therein. Extending forwardly from the front edge of each lid 211 is an elongate plunger 218. This is so positioned that when the lid 211 is raised (see FIG. 11) the plunger passes through the aperture 217 which also acts as an air inlet into the device. When the lid is in its lowered position the plunger 218 is protected from damage by upstanding walls 219 formed on the upper wall 216. As can be seen, the plunger 218 is curved, as viewed in side elevation, for reasons set out above.

The tray 202 defines a shallow chamber for receiving the rotatable support 203. The tray 202 can be moved in the housing between an inward position, as shown in FIG. 12, and an outward position, as shown in FIG. 11. Further outward movement beyond the above mentioned outward position is possible only on releasing a lug mechanism which, when released, makes it possible to remove the tray completely from the housing. The lug mechanism can be the same as that described above with reference to FIGS. 1 to 6, or FIGS. 7 and 8, and including a lug 23, as are details of the other internal components of the devices, and these are not therefore described in more detail here.

Extending from the front of the tray 202 is a mouthpiece 227. The mouthpiece is provided with a pair of apertures 228, though these are optional.

The remaining constructional details and the manner of use of the devices shown in FIGS. 10 to 12 can be ascertained from the above description of FIGS. 1 to 6, and FIGS. 7 and 8.

It will be apparent that two separate blister packs may be held in the article, one in each of the two devices. These two blister packs may contain different medicaments, and thus a patient needing two different medicaments can use a single article without the problem of needing repeatedly to change over the blister pack from one medicament to the other.

Figure 13:
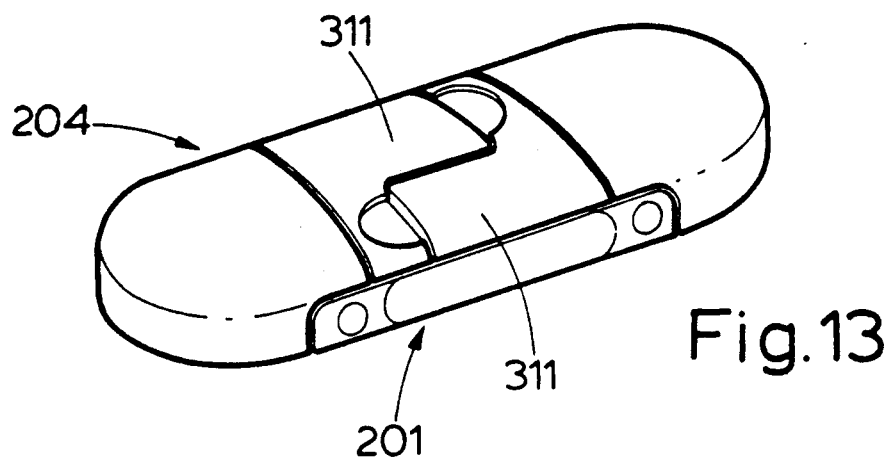
FIGS. 13 to 15 show a fourth embodiment of the invention, also for use in dispensing two medicaments, in positions corresponding to those FIGS. 10 to 12.
Figure 14:
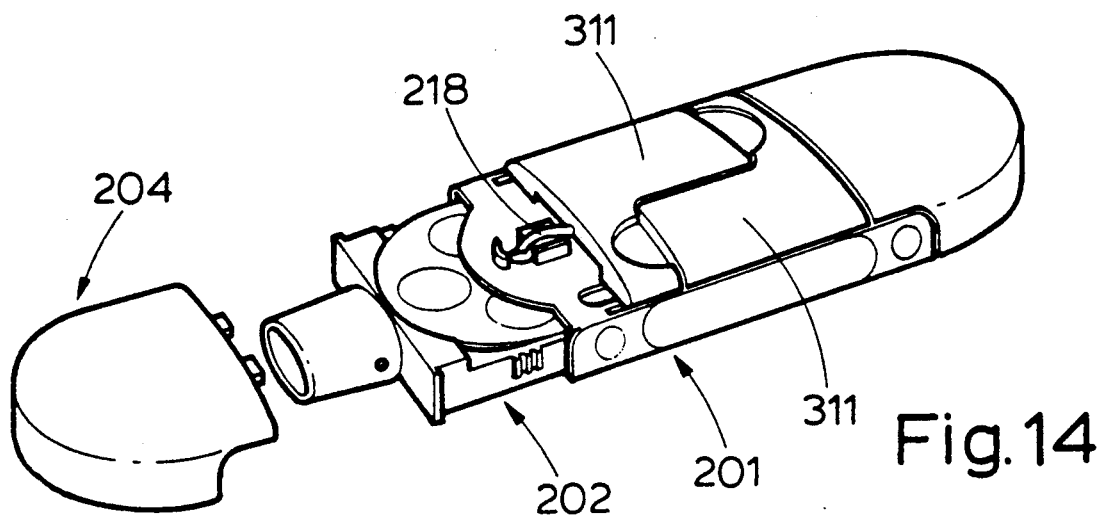
Figure 15:
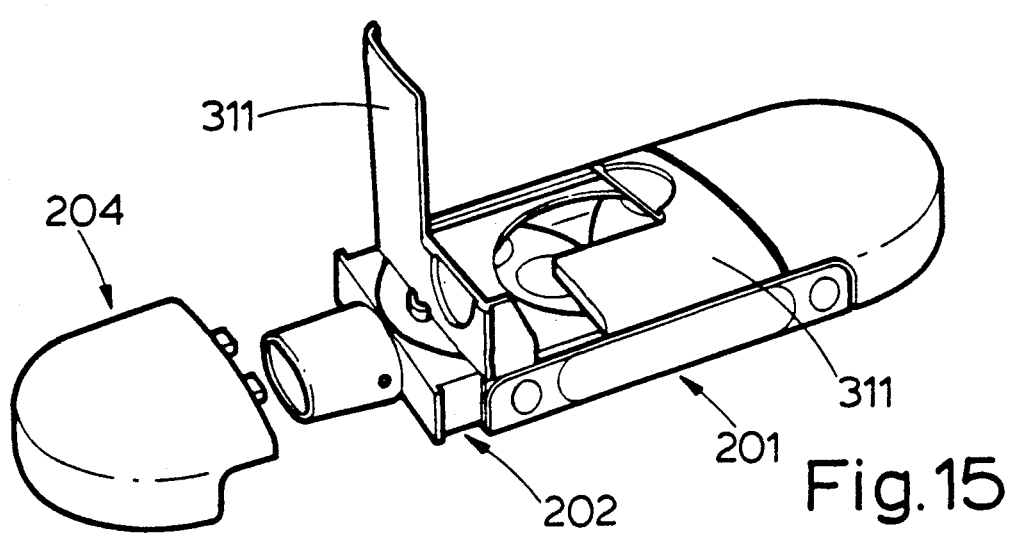

The embodiment shown in FIGS. 13 to 15 is identical to that shown in FIGS. 10 to 12 except as regards the lids. In the embodiment of FIGS. 13 to 15 the lids, denoted by reference numeral 311, each have the general shape of an L, with the stems of the two L's each occupying half the width of the article and being side by side with one another. This makes it possible for the distance between the distal end of each lid and the pivot thereof to be greater than is the case with the embodiment of FIGS. 10 to 12. This in turn means that for a given upward force applied by the patient to a lid the downward force of the tip of the plunger 218 will be greater in the embodiment of FIGS. 13 to 15 than it is in the embodiment of FIGS. 10 to 12. This in turn makes it easier for a patient to puncture a blister, a fact which may be of considerable significance to some patients, particularly the elderly and infirm.

We claim:

1. In a device for administering medicaments to patients, the medicaments being in solid finely divided form and enclosed within at least one puncturable container mounted on a carrier, said device comprising a housing which includes a base member and a lid pivotally mounted thereon for pivotal movement about an axis between a closed position and an open position and having a plunger connected thereto; the device further including a tray slidably mounted on said housing for movement between a first position in which the tray is substantially surrounded by the housing and a second extended position in which a portion of the tray is removed from said housing but the tray remains in contact with said housing, the tray further including a support on which said carrier is mounted; means for sliding the tray into its first position thereby bringing said one puncturable medicament container into registration with the plunger and means for pivotally moving said lid from its closed position to its open position thereby puncturing a medicament container while the tray is in its first position, said tray having an air inlet through which, in use, air enters the device and an outlet through which a patient inhales and whereby medicament is released from said one punctured container and entrained in an air flow produced by a patient.

2. A device according to claim 1, wherein the third tray has a third position in which the tray is completely removed from the housing.

3. A device according to claim 1, wherein the support is rotatably mounted on the tray to receive a carrier having a plurality of medicament containers arranged in a circle.

4. A device according to claim 3, wherein indexing means are provided operably by movement of the tray from its first to its second position and back to its first position to cause the support to be indexed to bring the next container into registration with the plunger.

5. A device according to claim 3, wherein the support is in the form of a disc having a plurality of apertures therethrough, the apertures being arranged in a circle so that each receives a respective medicament container.

6. A device according to claim 3, wherein the plunger is of such a length that it completely penetrates the container aligned therewith to produce an air flow passage therethrough and wherein the support has a plurality of ribs on a face thereof, the ribs cooperating with means provided on the housing adjacent the said outlet to define, together with said passage through the container, a substantially isolated air flow path which leads from the side of the container nearer the plunger, through the container and thence to the said outlet.

7. A device according to claim 1, wherein the support is adapted to receive a carrier having a single medicament container.

8. A device according to claim 7, further comprising a magazine adapted to receive at least one further carrier.

9. A device according to claim 1, wherein the plunger is located adjacent said axis.

10. A device according to claim 1, wherein the plunger is curved in a direction such as to reduce the size of hole which it produces in the container on penetration.

11. A device according to claim 1, wherein the carrier is a blister pack defining at least one blister as the said container.

12. A device according to claim 1, in combination with another such device to form an integral device.

13. A device according to claim 12, wherein said another such device is back-to-back in tandem with the first mentioned device.

14. A device according to claim 9, whereby the plunger is arranged to penetrate a container when the lid is moved to its open position and to leave the container when lid is moved from its open position towards its closed position.

* * * * *